United States Patent [19]

Schiller et al.

[11] 4,340,448

[45] Jul. 20, 1982

[54] POTENTIOMETRIC DETECTION OF HYDROGEN PEROXIDE AND APPARATUS THEREFOR

[75] Inventors: Julian G. Schiller, Pittsburgh; Lemuel B. Wingard, Jr., Monroeville, both of Pa.; Chung-Chiun Liu, Cleveland, Ohio

[73] Assignee: University of Pittsburgh, Pittsburgh, Pa.

[21] Appl. No.: 937,365

[22] Filed: Aug. 28, 1978

[51] Int. Cl.$^3$ .......................... C12Q 1/26; C12Q 1/30; G01N 27/46

[52] U.S. Cl. .................................. 204/1 T; 204/195 P; 204/195 B; 435/4; 435/14; 435/291; 435/817

[58] Field of Search ................ 204/195 B, 195 P, 1 E; 195/103.5 R, 103.5 C, 127; 128/2 E; 324/29; 435/291, 4, 14, 817

[56] References Cited

U.S. PATENT DOCUMENTS

| | | | |
|---|---|---|---|
| 2,850,359 | 9/1958 | Worthington et al. | 23/230 |
| 3,403,081 | 9/1968 | Rohrback et al. | 204/1 T |
| 3,539,455 | 11/1970 | Clark | 204/1 T |
| 3,542,662 | 11/1970 | Hicks et al. | 204/195 |
| 3,556,945 | 1/1971 | Messing | 195/63 |
| 3,595,755 | 7/1971 | Härtel | 195/103.5 |
| 3,666,733 | 5/1972 | Epton | 260/80.3 N |
| 3,707,455 | 12/1972 | Derr et al. | 204/195 P |
| 3,770,607 | 11/1973 | Williams | 204/195 P |
| 3,788,950 | 1/1974 | Hicks et al. | 195/103.5 R |
| 3,838,011 | 9/1974 | Hagen | 195/103.5 R |
| 3,838,033 | 9/1974 | Mindt et al. | 204/195 B |
| 3,839,154 | 10/1974 | Messing | 195/103.5 C |
| 3,841,971 | 10/1974 | Messing | 195/63 |
| 3,857,771 | 12/1974 | Sternberg | 204/195 B |
| 3,920,969 | 11/1975 | Berglas | 204/195 B X |
| 3,966,580 | 6/1976 | Janata et al. | 204/195 B |
| 4,024,042 | 5/1977 | Enfors et al. | 204/195 P |
| 4,055,175 | 10/1977 | Clemens et al. | 128/213 |

OTHER PUBLICATIONS

David A. Gough et al., Science, vol. 180, pp. 380–384, (1973).

J. N. Groves, General Electric Report No. 70-C-271, pp. 1–11, Nov. 1970.

S. P. Bessman et al., "Stabilized Glucose Oxidase Electrode for Monitoring Glucose in Biological Fluids", Methods and Instrumentation in Medical Engineering.

*Primary Examiner*—G. L. Kaplan
*Attorney, Agent, or Firm*—Buell, Blenko, Ziesenheim & Beck

[57] ABSTRACT

A method for potentiometric detection of hydrogen peroxide including providing an electrolytic cell having a working electrode and a reference electrode. The working electrode is composed of a hydrogen peroxide sensitive material and also is employed as a support for an oxidase enzyme. Introducing a hydrogen peroxide releasing substance into the cell and releasing the hydrogen peroxide by effecting interaction with the enzyme. Developing in said cell an electrical potential which is a function of the concentration of the hydrogen peroxide and measuring the electrical potential of the cell. The method may be employed as a quantitative glucose detector by employing as the enzyme or enzymes glucose oxidase with or without catalase.

Apparatus for potentiometric determination of hydrogen peroxide includes a cell containing an electrolyte, a working electrode and a reference electrode. An electrometer is operatively associated with the electrodes. The working electrode is composed of a material which will create an electrical potential when it interacts with hydrogen peroxide. At least one oxidase enzyme is immobilized on the working electrode.

13 Claims, 5 Drawing Figures

POTENTIOMETRIC DETECTION OF HYDROGEN PEROXIDE AND APPARATUS THEREFOR

BACKGROUND OF THE INVENTION

1. Field of the Invention

This invention relates to a potentiometric method and apparatus for determining quantitatively hydrogen peroxide concentration and, more specifically, in a preferred form, it relates to a means for determining glucose concentration through hydrogen peroxide analysis in a potentiometric manner.

2. Description of the Prior Art

A number of methods for determining hydrogen peroxide concentrations in various solutions have been known.

Among the known methods are the titrimetric methods using permanganate, ceric ion or iodometry. Of this group, the permanganate method has generally been considered the most accurate. A difficulty with this approach is the fact that the presence of certain interfering compounds which react with permanganate can interfere with the results. Included within the classes of interfering compounds are large quantities of halides, oxalate, aldehydes, salicylic acid and glycerine.

Gasometric analysis, which involves the measurement of evolved oxygen from the decomposition of hydrogen peroxide, has also been known.

Colorimetric methods may be based upon the reaction of hydrogen peroxide to form a colored peroxy compound, the oxidation of reduced dyes or metal-organic complexes, or the reduction of ferricyanide.

It has also been known to employ electrometric methods which are based on the polarographic technic. Hydrogen peroxide is reduced at a dropping mercury electrode at minus 1.2 V against a saturated calomel electrode. The reduced current is used as the indicator for hydrogen peroxide concentration in a solution.

It has also been known to employ various physical methods such as measuring the refractive index of the density of the solution. This can also be accomplished through ultraviolet spectrophotometry.

A number of these approaches as well as others are disclosed in patents and technical literature.

U.S. Pat. No. 3,838,033 discloses an enzyme electrode system which is amperometric in nature and relies on the use of a chemical reagent to serve as an acceptor in the enzymatic reaction. The use of redox dyes as acceptors is disclosed.

U.S. Pat. No. 3,595,755 also discloses a system wherein a chemical reagent is employed as an acceptor. Glucose determination is made as a result of hydrogen peroxide detected after interaction between glucose oxidase and galactose in the presence of iodide.

U.S. Pat. No. 3,770,607 discloses glucose determination apparatus wherein quinone is employed as an enzyme acceptor.

U.S. Pat. No. 3,539,455 discloses enzymes converting a polarographically inactive material into an active material. This system is an amperimetric system. Glucose oxidase is employed to convert glucose into gluconic acid and hydrogen peroxide. The use of a platinum electrode and a semi-permeable membrane are also disclosed.

Various methods of securing enzymes to supports have been disclosed. U.S. Pat. Nos. 3,841,971; 3,839,154 and 3,556,945 relate generally to measurement of changes in electrical conductivity as a result of enzymatic reaction in connection with glucose-glucose oxidase reactions. The use of adsorption, absorption, ion exchange, and covalent bonding are among the means of immobilization discussed. U.S. Pat. No. 3,666,733 discloses the use of acrylamide polymers to which enzymes are attached. See also U.S. Pat. No. 3,788,950 which discloses a system which requires the use of two identical or calibrated oxygen sensors and operates on the measurement of oxygen consumption principal. See also U.S. Pat. No. 3,542,662.

U.S. Pat. No. 3,838,011 relates to a system which measures oxygen produced or consumed.

U.S. Pat. No. 4,024,042 relates to an enzyme electrode with primary emphasis being directed toward such an electrode wherein the essential parts can be sterilized in an autoclave.

U.S. Pat. No. 2,850,359 relates to a unit for testing glucose and is primarily adapted to test for the presence of glucose in urine. The presence and amount of glucose are said to be indicated by color changes in a chromogenic oxygen acceptor.

U.S. Pat. No. 3,403,081 is directed primarily toward a gas detector adapted to be used in detecting poisonous gases and other elements. The reference electrode is said to be made of silver-silver chloride material and the sensor may be made from material such as platinum, nickel or carbon.

There remains, therefore, a need for a hydrogen peroxide quantitative detector which is economical to manufacture and use, provides very accurate readings and is adapted for miniaturization. There is further lacking such a system which is designed to provide potentiometric readout related to the hydrogen peroxide concentration.

SUMMARY OF THE INVENTION

The present invention has solved the above-described problems by providing a highly reliable, very sensitive detector and method which produces an electrical potentiometric output corresponding to hydrogen peroxide concentration. The apparatus and method are such as to be economical to adopt and use and the apparatus is adapted for miniaturization so as to increase its utility.

The method of the present invention includes providing an electrolytic cell which has a working electrode and a reference electrode. The working electrode is made of a material which is hydrogen peroxide sensitive. At least one oxidase enzyme is immobilized on the working electrode. Introducing a hydrogen peroxide releasing substance into the cell results in the enzymes causing the release of hydrogen peroxide which interacts with the working electrode to produce an electrical potential which is a function of the concentration of hydrogen peroxide in the solution. In one preferred form of the method glucose determination may be accomplished by the combined use of catalase and glucose oxidase as the enzymes employed. The working electrode may advantageously be a platinum screen which serves as both a support for the enzymes and a source of potential which is a function of the hydrogen peroxide concentration.

The apparatus of the present invention includes a cell containing an electrolyte, a working electrode and a reference electrode. An electrometer is operatively associated with the working electrode and the reference electrode to provide a reading of electrical potential. The working electrode is preferably composed of a material that creates a potential when it interacts with hydrogen peroxide. At least one oxidase enzyme is immobilized on the working electrode.

It is an object of the present invention to provide a method for quantitative determination of hydrogen peroxide through potentiometric means.

It is a further object of the present invention to provide such a method and an apparatus for practicing the method wherein a working electrode serves both as an enzyme support and as a source of electrical potential which is a function of hydrogen peroxide concentration.

It is a further object of the present invention to provide such apparatus which is readily adapted for miniaturization so as to be usable in vivo in patients.

It is yet another object of the present invention to provide such a method and apparatus which provides a reliable measure of glucose concentration.

These and other objects of the invention will be more fully understood from the following description of the invention on reference to the illustrations appended hereto.

DESCRIPTION OF THE PREFERRED EMBODIMENTS

Figure 1:
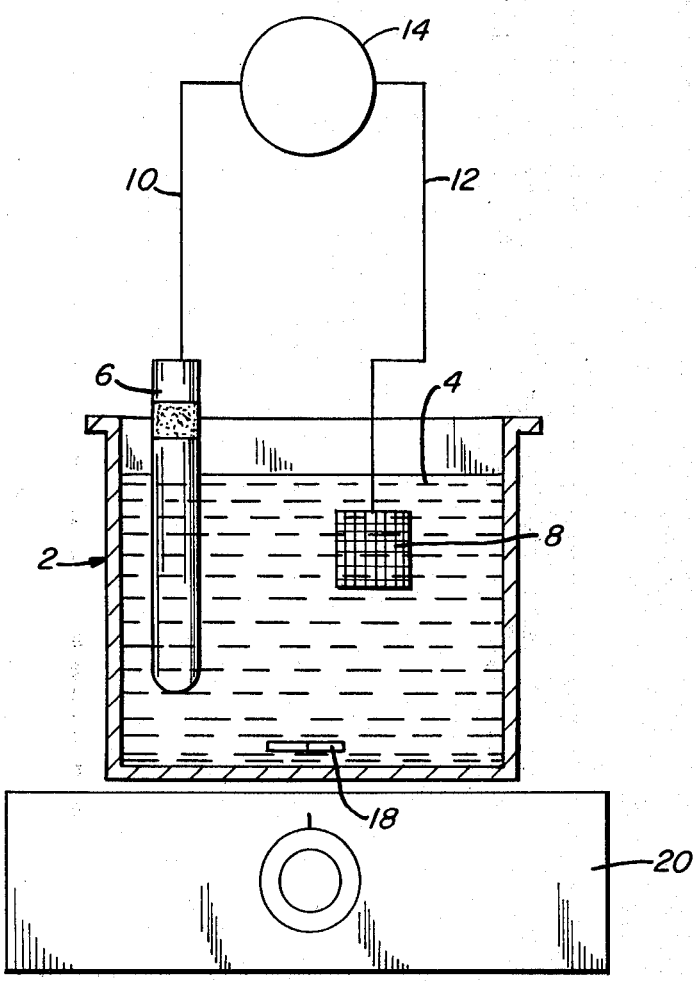
FIG. 1 is a schematic illustration of a form of apparatus of the present invention.

Referring now to FIG. 1 there is shown a schematic diagram of one form of apparatus of the present invention. As is shown in FIG. 1, an electrolytic cell 2 contains an electrolyte solution 4. A reference electrode 6 and a working electrode 8 are positioned within the cell 2 and are connected to electrometer 14 by electrical leads 10, 12. In the form shown in order to facilitate stirring, a stirring element 18 which in the form shown is a magnetic stirring element, is disposed within the cell 2 and an underlying stirrer base 20 adapted to establish movement through magnetic fields of magnetic stirring element 18 is shown.

For purposes of clarity of disclosure, a specific preferred form of cell and method will be disclosed herein, but it will be appreciated that other forms of methods and apparatus incorporating the primary features of the best mode disclosed herein may be employed without departing from the scope of the present invention.

A preferred form of the invention involves a system which will provide a potentiometric readout on electrometer 14 as a result of the potential difference created by hydrogen peroxide acting upon working electrode 8. The reference electrode 6 may conveniently be a silver-silver chloride electrode. The working electrode 8 is preferably composed of platinum or iridium. A preferred embodiment includes a working electrode 8 made from platinum screen material to which is secured an immobilized oxidase enzyme.

In the process of the present invention a hydrogen peroxide releasing substance is introduced into electrolyte 4 and interacts with the oxidase enzymes secured to the working electrode so as to release hydrogen peroxide which in turn interacts with support working electrode 8 to produce a potentiometric signal. This signal is a function of the concentration of the hydrogen peroxide in the electrolyte solution or, more specifically at the surface of the platinum screen. It will be appreciated that the hydrogen peroxide is a product of the enzymatic oxidation of glucose and has a concentration which is stoichiometrically proportional to the glucose concentration.

In one preferred form of the invention a glucose detector is provided. The enzymes glucose oxidase with or without catalase is immobilized on support working electrode 8. A glucose containing substance is introduced into the electrolyte 4 and interacts with the enzyme or enzymes to convert the glucose into gluconic acid and hydrogen peroxide. The catalase if present serves to convert most of the hydrogen peroxide into oxygen and water. The remaining hydrogen peroxide interacts with the support working electrode 8 to generate an electrical potential. This potential is a function of the glucose concentration and is proportional to the logarithm of the glucose concentration.

While a specific preferred enzyme glucose oxidase and catalase have been disclosed above it will be appreciated that other forms of oxidase enzymes (with or without catalase) may be employed in determining quantitatively hydrogen peroxide concentration, the invention is readily adapted to be employed with a wide range of oxidase enzymes including one or more of the enzymes set forth in the following group:

| E.C.# | Enzyme |
|---|---|
| 1.15.1.1 | Superoxide dismustase |
| 1.7.3.1 | Nitroethane oxidase |
| 1.4.3.1 | D-aspartate oxidase |
| 1.4.3.3 | D-amino acid oxidase |
| 1.4.3.2 | L-amino acid oxidase |
| 1.4.3.4 | Amine oxidase |
| 1.4.3.5 | Pyridox amine phosphate oxidase |
| 1.4.3.6 | Amine oxidase |
| 1.4.3.7 | D-glutamate oxidase |
| 1.4.3.8 | Ethanolamine oxidase |
| 1.2.3.3 | Pyruvate oxidase |
| 1.2.3.4 | Oxalate oxidase |
| 1.1.3.1 | Glycollate oxidase |
| 1.1.3.4 | Glucose oxidase |
| 1.1.3.5 | Hexose oxidase |
| 1.1.3.6 | Cholesterol oxidase |
| 1.1.3.7 | Aryl alcohol oxidase |
| 1.1.3.8 | L-gulonolactone oxidase |
| 1.1.3.9 | Golactose oxidase |
| 1.1.3.10 | Pyranose oxidase |
| 1.1.3.11 | L-Sorbose oxidase |
| 1.1.3.12 | Pyridoxine 4-oxidase |
| 1.1.3.13 | Alcohol oxidase |
| 1.1.3.15 | L-2-hydroxyacid oxidase |
| 1.3.3.1 | Dehydro-oratate oxidase |
| 1.3.3.2 | Lathosterol oxidase |
| 1.5.3.1 | Sarcosine oxidase |
| 1.5.3.2 | N-Methylamino acid oxidase |
| 1.5.3.4 | $N^6$-Methyl lysine oxidase |
| 1.5.3.5 | 6-hydroxy-L-nicotine oxidase |
| 1.5.3.6 | 6-hydroxy-D-nicotine oxidase |
| 1.8.3.2 | Sulphite oxidase |
| 1.10.3.5 | 3-hydroxyanthranilate oxidase |
| 1.2.3.1 | Aldehyde oxidase |
| 1.2.3.2 | Xanthine oxidase |

One preferred means of immobilizing the enzymes on the working electrode 8 is through use of a gel which permits oxygen and glucose to diffuse therethrough. One suitable gel is described by G. P. Hicks and S. J. Updike in Analytical Chemistry 38 (1966) 726. Another suitable gel is one prepared in the following fashion. The first five of the following six solutions are prepared in 0.1 M potassium phosphate buffer at pH 7.3 at room temperature and mixed in the volume shown and the sixth is provided in aqueous suspension.

|     |                                       | Volume Taken |
| --- | ------------------------------------- | ------------ |
| (1) | Acrylamide, 500mg/ML                  | 0.5ml        |
| (2) | Bisacrylamide, 23mg/ml                | 2.0ml        |
| (3) | Riboflavin, 0.1 milogram/ millimeter  | 0.25ml       |
| (4) | Ammonium Persulfate, 10mg/ml          | 0.25ml       |
| (5) | Glucose Oxidase (110 e.u./mg) (10mg/ml) | 0.50ml     |
| (6) | Catalase (41,397 e.u./mg) 6mg/ml in aqueous suspension | 0.10ml |
|     | Total                                 | 3.6ml        |

The final solution (3.6 ml) is gassed with 100% nitrogen for seven minutes at about 3–5 bubbles per second as introduced by a Pasteur pipet. The deoxygenated solution is transferred to a sandwich type Plexiglas mold that contains eight (1.5×1.5 cm) platinum screens. Each platinum screen is attached with lead wire. After the mold is filled, gel polymerization is initiated by placing the mold within 3 cm of a fifteen watt fluorescent bulb. Polymerization is completed within twenty minutes, at which time the gel coated screens are removed from the mold and stored at four degrees C. in 0.1 M potassium phosphate buffer until needed.

Although small variations in the amount of acrylamide and bisacrylamide may occur this has little effect on the functioning of the gel. It is desirable to avoid wide variations which could create an unstable gel i.e. too soft or no gel at all.

In using the glucose oxidase and catalase the amount of each enzyme incorporated into the gel can be varied extensively by holding the amount of one enzyme constant and varying the amount of the other enzyme. The amount of each enzyme and the ratio of the amount of one to the other is chosen to give the maximum slope and linearity of response from three to five hundred forty four mg/dl of glucose. For example, the ratio of catalase to glucose oxidase giving the maximum slope is approximately 1 mg of catalase to 0.4 mg glucose oxidase.

In a preferred form of the invention the electrode cell 2 is operated at a pH from about 5 to 9 with the preferred range being about 6.3 to 8.0.

While the gel means are disclosed herein as providing immobilization of the enzyme on the working electrode 8 as a preferred form, it will be appreciated that other forms including covalent coupling, difunctional cross linking, a semi-permeable membrane and adsorption may readily be employed.

Figure 2:
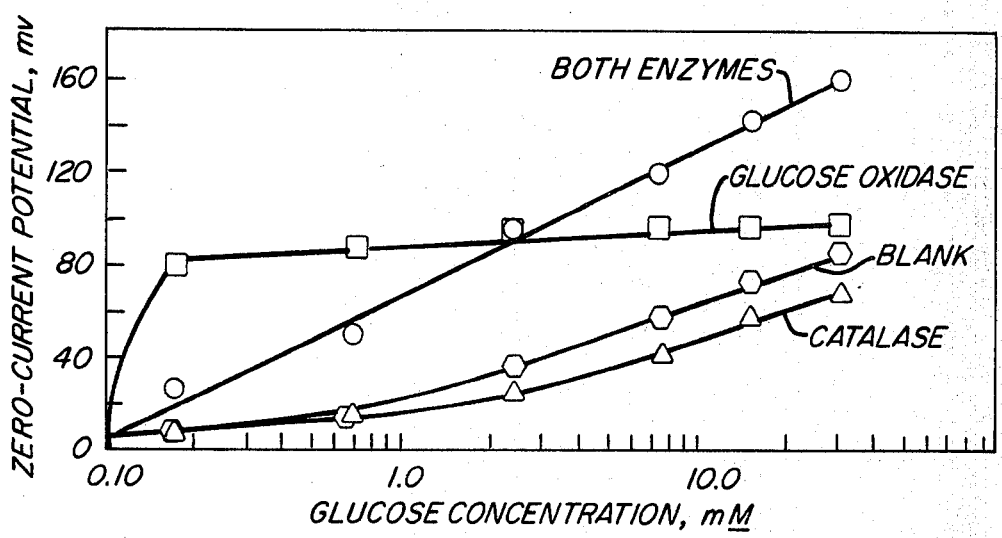
FIG. 2 is a plot of zero-current potential versus glucose concentration produced by the present invention and other approaches.

Referring now to FIG. 2, there is shown the zero-current potential in millivolts plotted against the glucose concentration in mM (in millimoles). This figure represents a plot of various systems into which glucose has been added. There is a blank specimen as a test, a second specimen with solely catalase being used, a third specimen with solely glucose oxidase being used and a fourth specimen with both catalase and glucose oxidase being used. It is noted that the plot of "BOTH ENZYMES" presents a nice linear relationship which permits ready conversion of electrical potential to glucose concentration. The glucose oxidase used alone provides less opportunity to distinguish different concentrations based on electrical potential particularly at the upper potential levels. The use of either the blank or catalase alone provided very little opportunity to distinguish concentrations between 0.10 and 1.0 mM concentrations.

Figure 3:
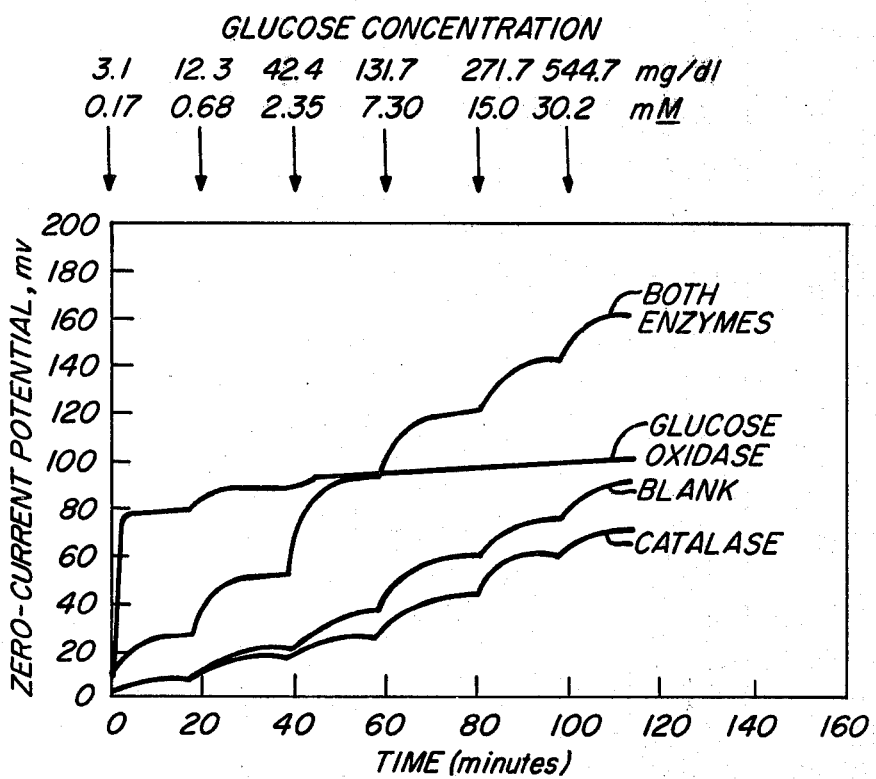
FIG. 3 is a plot of zero-current potential versus time as related to glucose concentration.

Referring now to FIG. 3, there is shown a plot of zero-current potential produced by sequential additions of glucose to enzyme electrodes. At the times shown on the plot, 0.6 ml aliquots of concentrated glucose solution were added to beakers containing enzyme electrodes and reference electrodes as described above in connection with FIG. 1. The final concentration of glucose is shown on the plot in terms of both mg% and molarity. The four plots show the use of no enzymes (blank), both enzymes (glucose oxidase, 2.3 e.u. and catalase, 1720 e.u.) or either enzyme alone (glucose oxidase, 2.3 e.u. or catalase 1720 e.u.). It is noted that in this figure also, ready precise conversion of the electrical potential readout to glucose concentration is permitted with the preferred use of both enzymes. The use of glucose oxidase alone does not permit as accurate conversion and the use of either blank or catalase alone does not permit ready conversion in the lower ranges.

Figure 4:
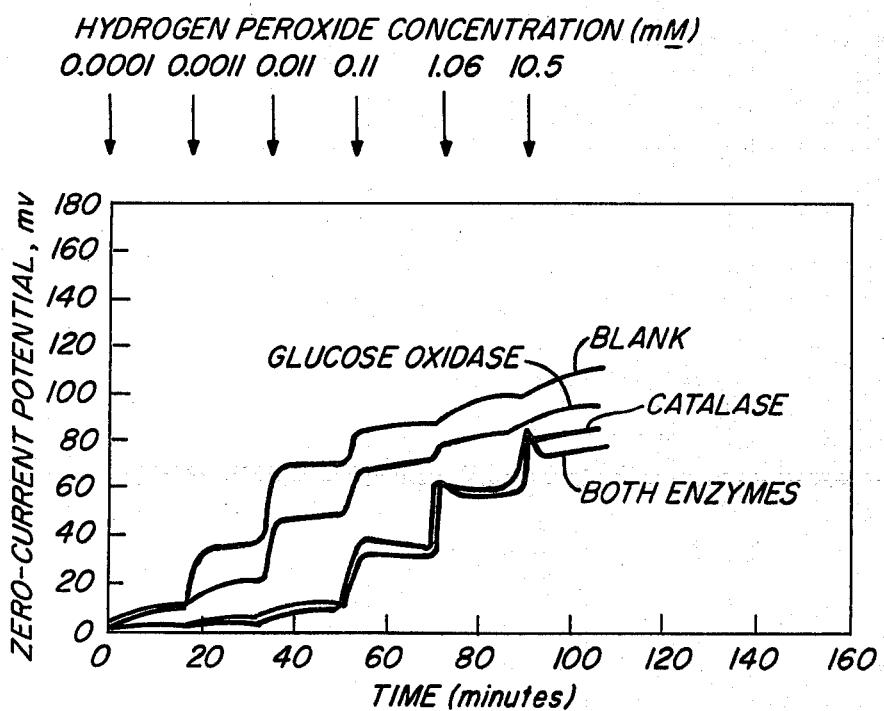
FIG. 4 is a plot of zero-current potential versus time as related to hydrogen peroxide concentration for the present invention and other approaches.

As has been stated previously, while the present method and apparatus are uniquely suited to effective potentiometric quantitation of glucose concentration, it is more broadly applicable to determinations of hydrogen peroxide concentration regardless of source of the hydrogen peroxide. Referring now to FIG. 4 there is a plot of zero-current potential versus time and actual hydrogen peroxide concentration. At the times shown on the graph 1.4 ml aliquots of concentrated hydrogen peroxide solutions were added to the beakers containing enzyme electrodes and reference electrodes of the type described in connection with FIG. 1. The final concentration of hydrogen peroxide is shown in terms of molarity. The respective enzyme electrodes contain no enzymes (blank), both enzymes (glucose oxidase 2.3 e.u. and catalase 1720 e.u.) or either enzyme alone (glucose oxidase, 2.3 e.u. or catalase 1720 e.u.).

Figure 5:
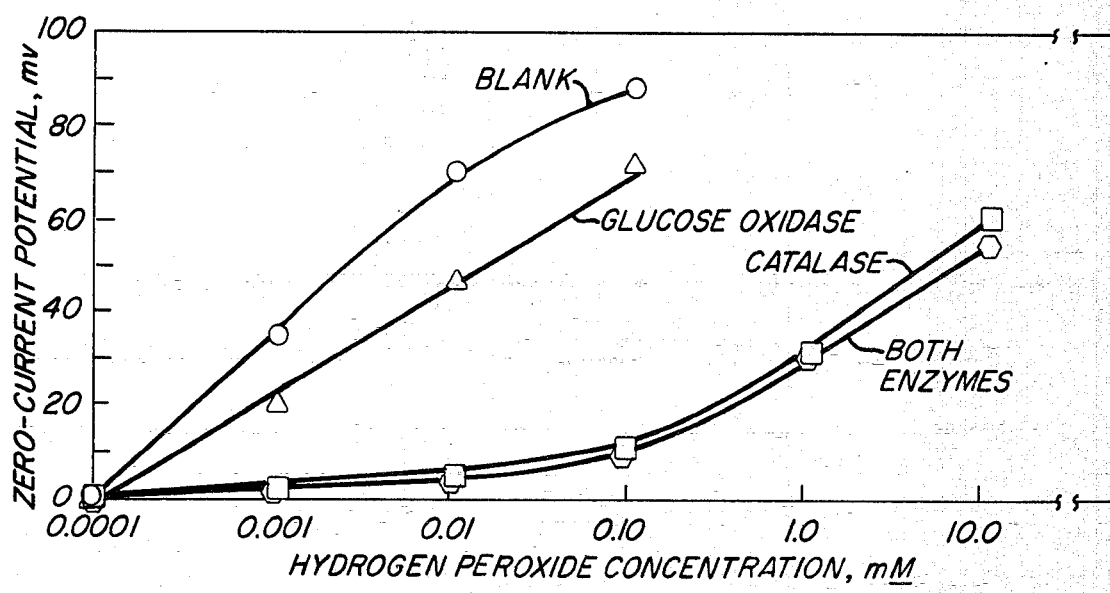
FIG. 5 is a plot of zero-current potential versus hydrogen peroxide concentration for the present invention and other approaches.

FIG. 5 is a semi-logarithmic plot of zero-current steady state potential (mv) versus hydrogen peroxide concentration mM for the four enzyme conditions. The values for the steady state potentials obtained in FIG. 3 were measured fifteen minutes after the addition of hydrogen peroxide.

While for convenience of reference and clarity of disclosure certain specific forms of enzymes and support materials have been described in detail along with certain preferred solution pH ranges and other method parameters, it will be appreciated that variations will become apparent to those skilled in the art while still remaining within the scope of the present invention. For example, other sources of hydrogen peroxide might be employed. Also, one may provide other means of immobilizing the enzymes on the working electrode which serves as both a support and as a potential generating means. Also, while a meter form of readout for the electrical potential has been shown, it will be appreciated that in lieu of or in addition to the visual readout other means may be employed including a graph recorder, a monitoring system adapted to emit an alarm when predetermined set points have been violated or coaction with the computerized system involved with automatic systems such as patient monitoring systems adapted to supply insulin or glucose to diabetics. See U.S. Pat. No. 4,055,175.

Whereas particular embodiments of the invention have been described above for purposes of illustration, it will be evident for those skilled in the art that numerous variations of the details may be made without departing from the inventions as defined in the appended claims.

What is claimed:

1. A method for potentiometric detection of hydrogen peroxide comprising
    providing an electrolytic cell having a reference electrode and a working electrode composed at least in part of a hydrogen peroxide sensitive material,
    immobilizing at least one oxidase enzyme on said working electrode,
    said immobilized enzyme including catalase,
    introducing a hydrogen peroxide releasing substance into said cell,
    releasing said hydrogen peroxide by effecting contact between said enzyme and said hydrogen peroxide releasing substance,
    developing in said cell through interaction between said hydrogen peroxide and said working electrode an electrical potential which is a function of the concentration of said hydrogen peroxide in said electrolytic cell,
    maintaining the pH of said cell in the range of about 5 to 9, and
    measuring said electrical potential of said cell whereby said working electrode will serve as a support for said oxidase enzyme and also as a hydrogen peroxide sensitive electrode to provide an electrical potential signal which is a function of the concentration of said hydrogen peroxide.

2. The method of claim 1 including
    providing glucose in said hydrogen peroxide releasing substance,
    reducing said glucose to gluconic acid and hydrogen peroxide, and
    operating said cell at a pH of about 6.3 to 8.0.

3. The method of claim 1 including immobilizing at least one said oxidase enzyme selected from the group consisting of Superoxide dismutase, Nitroethane oxidase, D-aspartate oxidase, D-amino acid oxidase, L-amino acid oxidase, Amine oxidase, Pyridox amine phosphate oxidase, Amine oxidase, D-glutamate oxidase, Ethanolamine oxidase, Pyruvate oxidase, Oxalate oxidase, Glycollate oxidase, Glucose oxidase, Hexose oxidase, Cholesterol oxidase, Aryl alcohol oxidase, L-gulonolactone oxidase, Golactose oxidase, Pyranose oxidase, L-Sorbose oxidase, Pyridoxine 4-oxidase, Alcohol oxidase, L-2-hydroxyacid oxidase, Dehydro-oratate oxidase, Lathosterol oxidase, Sarcosine oxidase, N-Methylamino acid oxidase, $N^6$-Methyl lysine oxidase, 6-hydroxy-L-nicotine oxidase, 6-hydroxy-D-nicotine oxidase, Sulphite oxidase, 3-hydroxyanthranilate oxidase, Aldehyde oxidase, and Xanthine oxidase.

4. The method of claim 1 wherein said immobilized enzyme includes glucose oxidase.

5. The method of claim 1 including immobilizing said enzyme on said working electrode by providing said enzyme in a gel which is cast on said working electrode, whereby said working electrode will serve as both a support and a source of an electrical potential signal corresponding to hydrogen peroxide concentration.

6. The method of claim 5 including employing a gel which permits oxygen and glucose to diffuse therethrough.

7. The method of claim 1 including providing said working electrode of a platinum screen.

8. The method of claim 1 including reducing a portion of said hydrogen peroxide to oxygen and water by means of said catalase.

9. An apparatus for potentiometric detection of hydrogen peroxide comprising
    a cell containing an electrolyte, a working electrode and a reference electrode,
    an electrometer operatively associated with said working electrode and said reference electrode,
    said working electrode composed of a material which creates an electrical potential when it interacts with hydrogen peroxide,
    at least one oxidase enzyme immobilized on said working electrode,
    said enzyme includes glucose oxidase and catalase,
    whereby introduction of a hydrogen peroxide containing substance into said cell will result in said enzyme releasing hydrogen peroxide from said hydrogen peroxide releasing substance with the hydrogen peroxide interacting with said working electrode and said working electrode functioning as a support for said oxidase enzyme and to generate an electrical potential which is a function of the concentration of said hydrogen peroxide.

10. The apparatus of claim 9 wherein said working electrode is a platinum screen.

11. The apparatus of claim 9 including said enzymes being immobilized by being secured to said working electrode by a gel.

12. The apparatus of claim 9 including said enzymes including at least one enzyme selected from the group consisting of Superoxide dismutase, Nitroethane oxidase, D-aspartate oxidase, D-amino acid oxidase, L-amino acid oxidase, Amine oxidase, Pyridox amine phosphate oxidase, Amine oxidase, D-glutamate oxidase, Ethanolamine oxidase, Pyruvate oxidase, Oxalate oxidase, Glycollate oxidase, Glucose oxidase, Hexose oxidase, Cholesterol oxidase, Aryl alcohol oxidase, L-gulonolactone oxidase, Golactose oxidase, Pyranose oxidase, L-Sorbose oxidase, Pyridoxine 4-oxidase, Alcohol oxidase, L-2-hydroxyacid oxidase, Dehydro-oratate oxidase, Lathosterol oxidase, Sarcosine oxidase, N-Methylamino acid oxidase, $N^6$-Methyl lysine oxidase, 6-hydroxy-L-nicotine oxidase, 6-hydroxy-D-nicotine oxidase, Sulphite oxidase, 3-hydroxyanthranilate oxidase, Aldehyde oxidase, and Xanthine oxidase.

13. The apparatus of claim 9 including said electrolyte having a pH of about 5 to 9.

* * * * *

UNITED STATES PATENT AND TRADEMARK OFFICE
CERTIFICATE OF CORRECTION

PATENT NO. : 4,340,448
DATED : July 20, 1982
INVENTOR(S) : JULIAN G. SCHILLER, LEMUEL B. WINGARD, JR. and CHUNG-CHIUN LIU It is certified that error appears in the above-identified patent and that said Letters Patent are hereby corrected as shown below:

Column 6, lines 12-13, "solution" should be --solutions--.

Column 6, line 44, delete the comma (,) after "oxidase".

Signed and Sealed this

Thirtieth Day of November 1982

[SEAL]

Attest:

GERALD J. MOSSINGHOFF

Attesting Officer

Commissioner of Patents and Trademarks